(12) United States Patent
Smith (10) Patent No.: US 10,092,450 B2
(45) Date of Patent: Oct. 9, 2018

(54) ZERO PARALLAX VISUAL AXIS GLASSES FOR CORNEAL PRE-MARKING

(71) Applicant: Dan Smith, Rapid City, SD (US)

(72) Inventor: Dan Smith, Rapid City, SD (US)

(73) Assignee: Dan Smith, Rapid City, SD (US)

( * ) Notice: Subject to any disclaimer, the term of this patent is extended or adjusted under 35 U.S.C. 154(b) by 0 days.

(21) Appl. No.: 15/351,364

(22) Filed: Nov. 14, 2016

(65) Prior Publication Data

US 2017/0231820 A1    Aug. 17, 2017

Related U.S. Application Data

(60) Provisional application No. 62/255,350, filed on Nov. 13, 2015.

(51) Int. Cl.
| | | |
|---|---|---|
| *A61B 3/10* | (2006.01) | |
| *A61F 9/013* | (2006.01) | |
| *A61B 3/00* | (2006.01) | |
| *A61B 3/14* | (2006.01) | |

(52) U.S. Cl.
CPC .......... *A61F 9/0136* (2013.01); *A61B 3/0091* (2013.01); *A61B 3/10* (2013.01); *A61B 3/145* (2013.01)

(58) Field of Classification Search
CPC ....... A61B 3/1015; A61B 3/14; A61B 3/0091; A61B 3/0025; A61B 3/103
USPC .......................... 351/211–216, 227, 233, 246
See application file for complete search history.

(56) References Cited

U.S. PATENT DOCUMENTS

| | | | |
|---|---|---|---|
| 8,328,357 B2 * | 12/2012 | Davis ....................... | A61B 3/13 351/215 |
| 2006/0200013 A1 * | 9/2006 | Smith ................ | A61B 5/14532 600/319 |

* cited by examiner

*Primary Examiner* — Mohammed Hasan
(74) *Attorney, Agent, or Firm* — Corridor Law Group, P.C.

(57) ABSTRACT

Zero parallax visual axis glasses for corneal pre-marking include a target light, an alignment light, a polarized lens and a short pass filter. In some embodiments the targeting light and/or alignment light are LEDs and/or configured to blink. In some embodiments the target light is red. In certain embodiments the alignment light is white. The polarized lens can be placed on a user's non-dominant eye and block light originating from the target light and/or alignment light. The short pass filter can be configured to allow light from the target light to only pass through in one direction.

15 Claims, 7 Drawing Sheets

ZERO PARALLAX VISUAL AXIS GLASSES FOR CORNEAL PRE-MARKING

CROSS-REFERENCE TO RELATED APPLICATION(S)

This application is related to and claims priority from U.S. provisional application No. 62/255,350 filed on Nov. 13, 2015 entitled "Zero Parallax Visual Axis Glasses For Corneal Pre-Marking". The 62/255,350 application is hereby incorporated by reference in its entirety

FIELD OF THE INVENTION

The present invention relates to eye surgery and more specifically to pre-marking for ophthalmic surgical procedures.

BACKGROUND OF THE INVENTION

The cornea is responsible for approximately two-thirds of the refractive (light bending) power of the human eye. This is largely due to the high refractive index at the air/tear film interface. The crystalline lens (located between the cornea and the retina) is responsible for the other third of the eye's total refractive power. In effect, each eye contains two lenses that act to bend or focus light coming into the eye: the cornea and the crystalline lens.

Astigmatism is a condition in which the shape of a lens is warped so that it is steeper across one meridian and flatter across another. Modern visualization and mapping techniques can measure the deformation of the cornea. Corneal distortion is caused by one section of the cornea being flatter than another. Such distortion is commonly symmetric. That is, if a fine line were drawn across a cornea where the cornea was flattest, the cornea would be most sharply curved on a line perpendicular to the first line. This warping distorts and blurs an individual's vision. While astigmatism is generally caused by a deformation of the cornea, it can also be present within the crystalline lens.

For decades surgeons have been replacing the natural lenses of patients' eyes with intraocular lenses (IOLs) to deal with astigmatism and other visual maladies. IOLs are usually made of a compound such as silicone or acrylic plastics. When an IOL is implanted, the eye is termed "pseudophakic".

During refractive cataract surgery a surgeon removes a cataractous lens which is cloudy or opaque and often will attempt to correct preexisting vision problems such as myopia, hyperopia or astigmatism. Ideally after cataract surgery the patient will no longer need contacts or glasses for the operated eye(s).

Surgeons also correct corneal astigmatism and/or cataracts using Toric IOLs which offer both spherical and cylindrical corrections. IOLs are also used to correct other optical refractive errors such as presbyopia. For example, accommodating or multifocal IOLs can be used to restore reading vision. These lenses traditionally require the correction of corneal astigmatism to work best.

Other implants for correcting vision are multifocal IOLs and corneal inlays. Both of these implants are designed to offer better accommodation, usually for close range focus. Corneal inlays are placed in a pocket created in the cornea by a laser and create an increased depth of field for the patient. Near perfect alignment of the implant (which is often needed or desired for the outcome to be beneficial) requires modern techniques.

When astigmatism is corrected using a Toric IOL, the IOL is shaped to counteract the distortion of the cornea. In order for this correction to properly occur, the IOL is turned or rotated to a position, which is aligned with the corneal astigmatism and preferably centered relative to the patient's visual axis.

Modern surgical procedures intending to correct or enhance an individual's visual acuity rely on the overall accuracy the surgeon is able to place with his or her incisions, tissue ablations, implants and/or sutures. In order for an IOL to work properly, it should be accurately aligned with the cornea. If the IOL is improperly aligned with the corneal astigmatic meridians (often only by a few degrees), the patient's vision will likely be suboptimal. Many corneal inlays require axis accuracy with error no greater than 0.3 mm decentered from the visual axis. A misalignment of 5 degrees can cost the patient 15 percent of the desired effect. Therefore, it is important that astigmatic correcting IOLs be properly aligned with the patient's corneal aberrations.

Most IOLs have two small supports called haptics which engage the peripheral capsule (fornices). The haptics hold the IOL in place so that it does not rotate within the eye while at the same time centering the optic within the pupil. Once an IOL has been placed in the eye, the haptics bind to the interior of the eye by fibrosis of the capsular bag making it difficult, if not impossible, to reposition the IOL. Often the only solution for a misaligned IOL is an IOL exchange which can lead to a host of complications.

When implanting an IOL or a similar device, surgeons often place pre-operative marks on the cornea to aid in the alignment and implantation of IOLs as it is often difficult to see whether the IOL is aligned properly with the visual axis of the optic system.

Traditional pre-marking systems rely on the patient fixating on a given object (traditionally the ear of the surgeon or another object behind the surgeon). This method is prone to error as it is extremely difficult, if not impossible, to correctly align the IOL with the patient's visual axis using this technique.

As stated above, proper alignment of these IOLs and similar devices can be important, if not crucial, for optimum, or at least satisfactory, optical results. Toric IOLs, accommodating IOLs, multi-focal IOLs and simple spherical IOLs benefit from proper centration and alignment. Future advances in IOL development such as Higher Order Aberration (HOA) correcting lenses will also depend heavily on near perfect alignment. Current pre-marking methods fail to orient the corneal reference marks with the patient's visual axis (the center line of the optical path) as the origin.

SUMMARY OF THE INVENTION

Shortcomings of existing devices for corneal pre-marking are overcome by zero parallax visual axis glasses for corneal pre-marking. In some embodiments, the glasses comprise:
 (a) a target light;
 (b) at least one alignment light;
 (c) a polarized lens; and
 (d) a short pass filter.

In some embodiments, the target light is a light emitting diode (LED). In some preferred embodiments, target light is red. In some embodiments, the target light can be configured to blink.

In some embodiments, the alignment light is an LED. In some preferred embodiments, the alignment light is white. The alignment light can be configured to blink.

In some embodiments, the polarized lens is configured for placement over a user's non-dominant eye. The polarized lens can be configured to block light originating from the alignment light. The polarized lens can be configured to block light originating from the target light.

In some embodiments, the short pass filter is configured to prevent, or at least reduce, light originating from the targeting light from reaching a user.

In some embodiments, the marking glasses are configured to fit over a pair of traditional prescription glasses.

In a preferred embodiment, the zero parallax visual axis glasses for corneal pre-marking comprise:
  (a) a target light;
  (b) four alignment lights;
  (c) a polarized lens; and
  (d) a short pass filter.

In the foregoing embodiment, the four alignment lights can be configured to form a cross. The target light can be an LED. In some preferred embodiments, the target light is red. The target light can be configured to blink.

DETAILED DESCRIPTION OF ILLUSTRATIVE EMBODIMENT(S)

The utilization of illuminating lights and modern filter coatings offer the application of point light sources in a manner that allows patients to fixate on a target aligned precisely with that of the user. A flashing light can be aligned with the user's visual axis so that when the patient fixates on this target the user and the patient are on the same axis. Thus the user's dominant eye and the patient's eye that is the subject of the surgery are aligned along one path. This target does not obstruct the user's line of sight while centering on the patient's visual axis.

This flashing light is aligned with the user's view through the dominant eye ocular and is intended to provide an "on-axis" fixation for the patient. The flashing LED is easily distinguished by the patient and is easy to focus upon. The patient can comfortably look directly at this target, and as such vertical and horizontal references are reflected back to the user's dominant eye. These vertical/horizontal reflections provide centering references for the user to accurately align marking glasses suited for the procedure.

In some embodiments, the light in an LED. In other or the same embodiments, the light is a red LED.

Glasses that provide parallax free alignment allow a user to pre-mark the cornea for a given procedure. The marks align accurately with the patient's visual axis.

The illuminated target for the patient to fixate his or her eye and four illuminating LEDs placed vertical and horizontal (denoted cardinal references in corneal surgery applications) about the fixation target, can act as reference points during pre-marking. In some embodiments, the illuminated target is a red flashing LED that provides an easy subject for the patient to locate and maintain focus. This target LED holds the patient's focus in line with the user's visual axis while the use pre-marks the patient.

This targeting LED is not visible to the user or technician while in use. This allows for an unobstructed view of the patient's eye during pre-marking. Because the user cannot see the target LED, he or she can clearly mark the cornea with the reflecting vertical and horizontal reference LEDs centered with the crosshairs or centering hub of the marker.

Because the user and the patient are viewing one another on one simultaneous visual axis pathway, pre-marking is essentially centered to the patient's visual axis. This provides optimal, or at least satisfactory, centering of implants and procedures during surgery so the integrity of the optical system is improved and the full potential of the correcting or enhancing procedure is achieved.

In addition, the method reduces, if not eliminates parallax; as users cannot cross fixate while utilizing stereo optics. Stereo optics provide depth of field for the user so the marking instrument's contact with the cornea is controlled. The user's non-dominant eye views only the cornea, with no target or alignment LEDs visible. The uniqueness of the reflecting LEDs seen from the patient's cornea by the dominant eye of the user helps aid in creating a parallax-free, or at least a reduced-parallax, alignment of the patient's visual axis. With the patient fixating upon a centration light, the pre-marks can be placed in optimal alignment with respect to the vertical and horizontal axes and most importantly centered on the user's and patient's visual axes.

Figure 1:
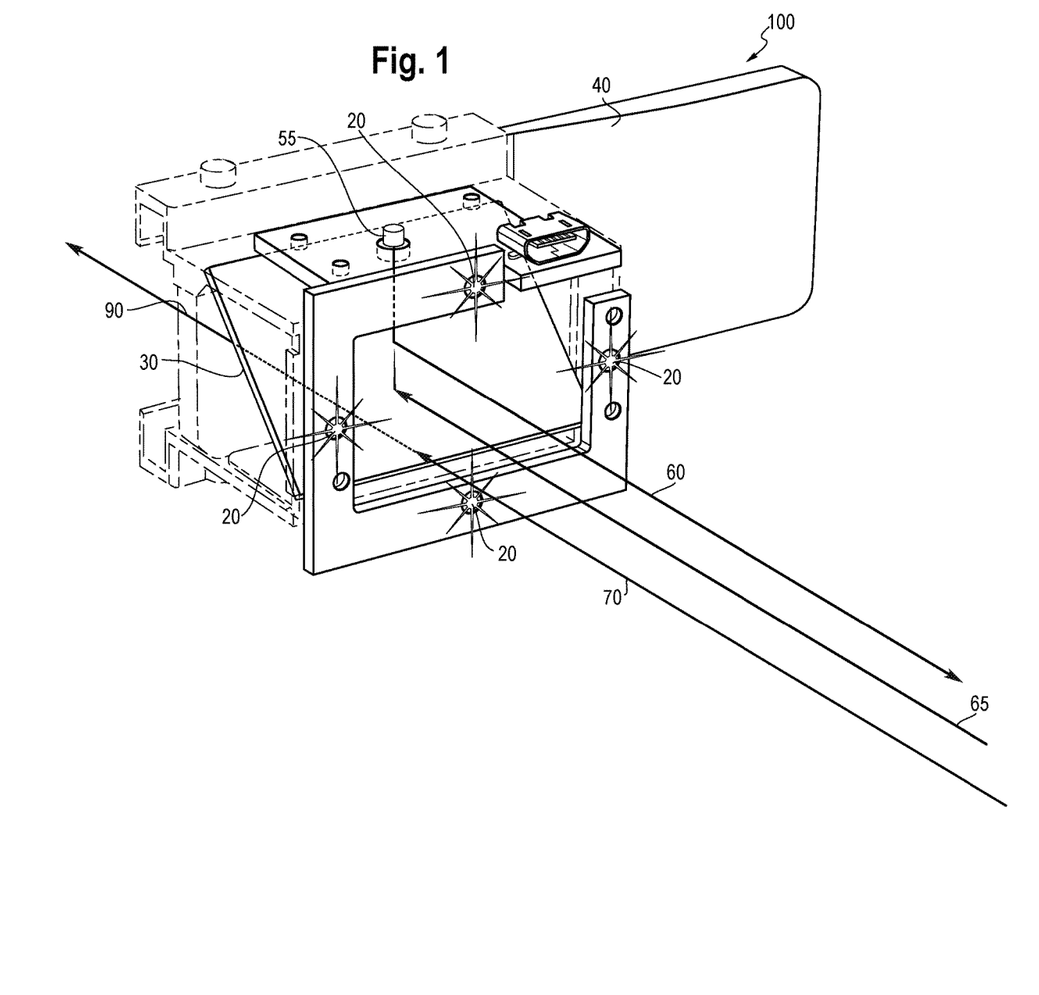
FIG. 1 is a cutaway perspective view of the top of an example embodiment of a pair of marking glasses.

FIG. 1 is cutaway perspective view of the top of marking glasses 100.

In the shown embodiment, marking glasses 100 has four alignment lights 20. In some embodiments, alignment lights 20 are LED lights. In other or the same embodiments, alignment lights 20 are white. In certain embodiments, alignment lights 20 are configured to blink. It is important to note that marking glasses 100 can have various numbers of alignment lights 20. In other embodiments, alignment lights 20 can be different shapes and/or sizes, such as an illuminated "x" or a small ring light, which can give the light reflex a geometric shape, further facilitating centration of markers and/or improving illumination.

In FIG. 1, alignment lights 20 act as vertical and horizontal references for the user while target 50 allows the patient to fixate on a given point. This allows the patient's visual axis to be aligned directly with the visual axis of the user's dominant eye, namely, the eye over which marking glasses 100 is normally configured to be worn.

FIG. 1 shows the orientation of short pass filter 30 that has its wavelength selected to allow for transmission of light from target light 55 (target-light ray 60) while minimizing, or at least reducing, the impact of target-light ray 65 on the user. In some embodiments, nearly all of the light emitted from target light 55 is transmitted to the patient but blocked from user by short pass filer 30. Short pass filter 30 allows other light waves (ray 70) including light from alignment lights 20 to pass to user for full visibility of the patient's eye with the exception of the small color spectrum reduced, if not eliminated, by filter 30.

Figure 2:
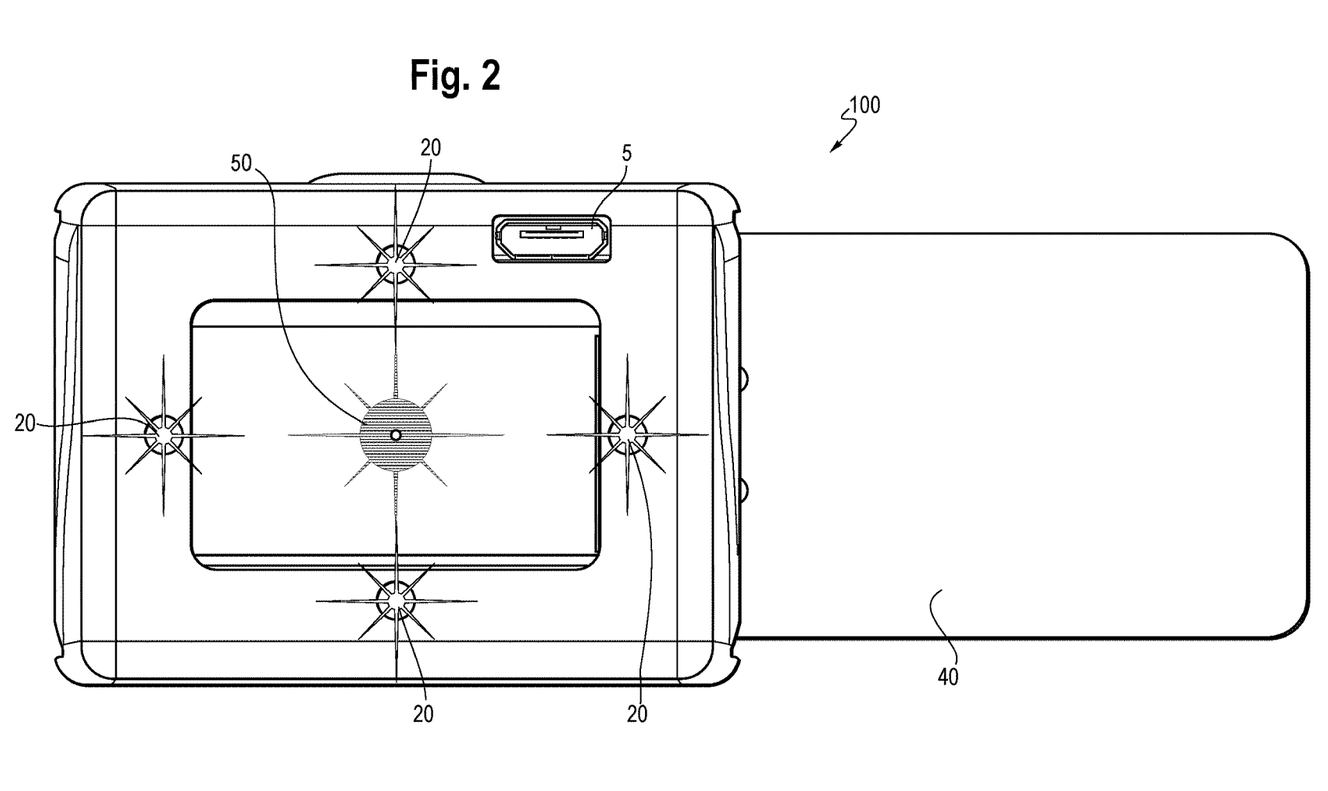
FIG. 2 is a front elevation view of an example embodiment of a pair of marking glasses.

FIG. 2 is a front elevation of marking glasses 100 and is the view a patient undergoing a procedure would see of marking glasses 100.

FIG. 2 also shows target 50. Target 50, as show in FIG. 1, is actually a reflection coming from target light 55 which is directly above and behind target 50 and is reflected off short pass filter 30 (see FIG. 2). In certain embodiments, target light 55 is a LED. In other or the same embodiments, target light 55 is red.

Marking glasses 100 provides accurate centration of pre-operative corneal marks when properly aligning the chosen pre-marking instrument with the patient's corneal light reflex (Purkinjie-Sanson image) of the vertical and horizontal reference lights.

Figure 3:
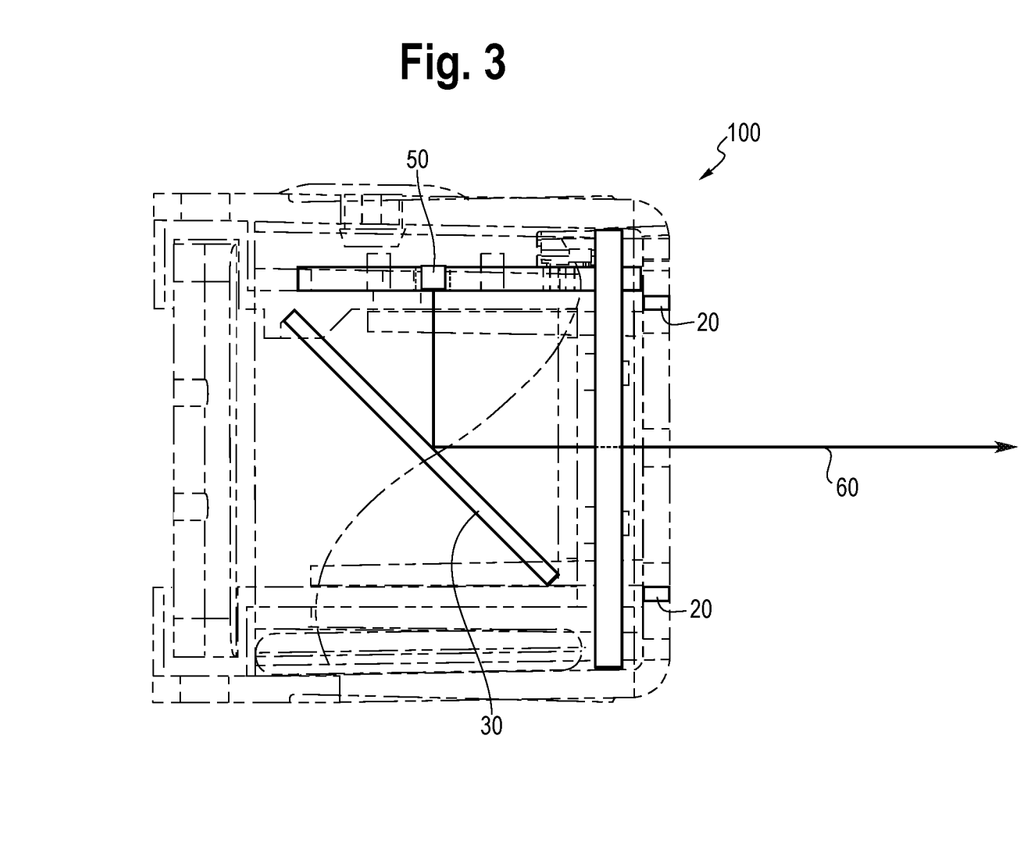
FIG. 3 is a cutaway side view of an example embodiment of a pair of marking glasses.

FIG. 3 is a cutaway side view of marking glasses 100. It shows the 90° angle, one-way path 60 of target light 55 that a patient fixates his or her vision. This is in line with the user's visual axis during pre-marking.

Figures 4A, 4B:
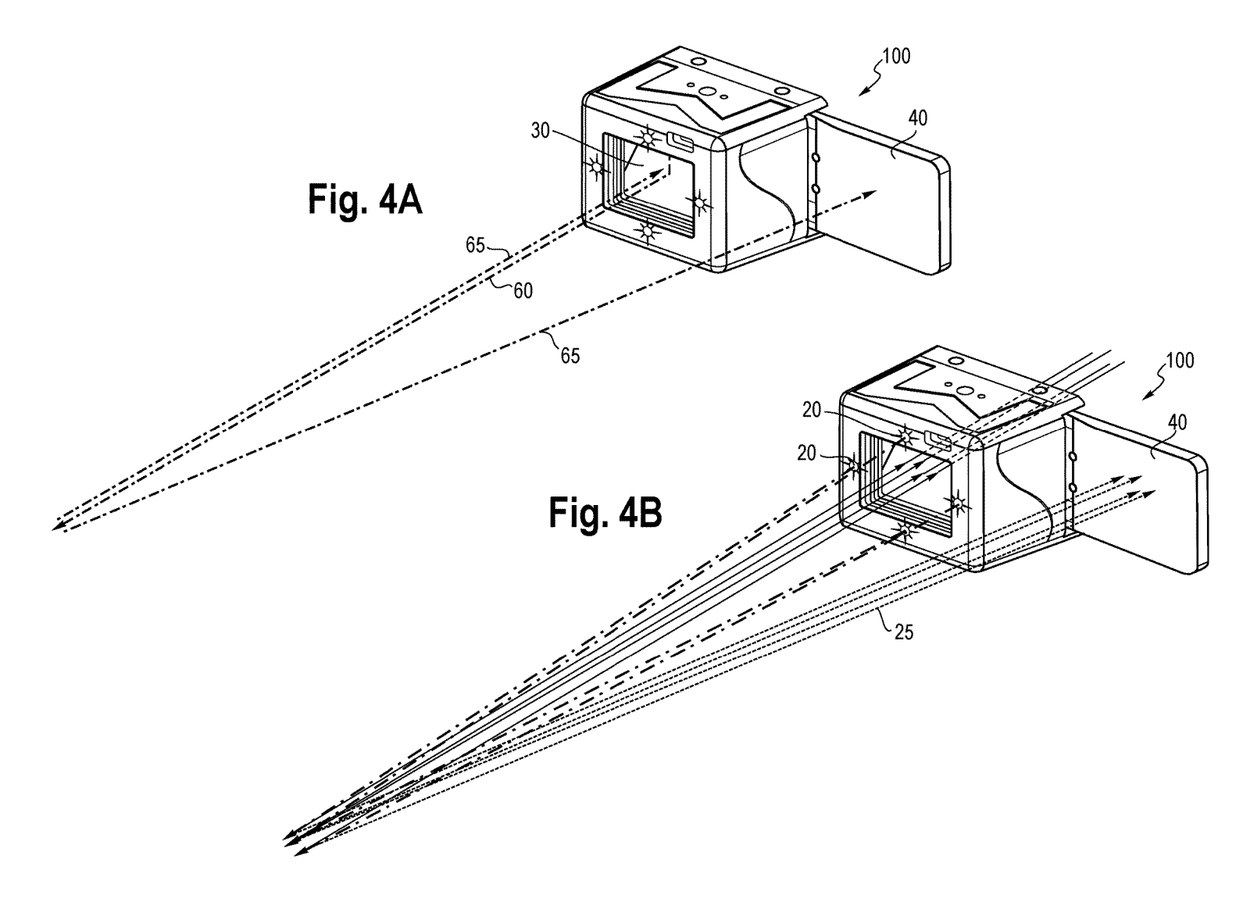
FIGS. 4A and 4B are perspective views showing the paths of light emitted and viewed with marking glasses.

FIGS. 4A and 4B are perspective views showing the paths of light emitted and viewed with marking glasses 100.

FIGS. 4A and 4B show polarized lens 40 and marking glasses 100 configured for a right-eye dominant user. Polarized lens 40 covers the non-dominant eye of the user to eliminate, or at least reduce, the user's visibility of either target light 55 (via ray 65) and/or alignment lights 20 (via rays 25). In some embodiments, this effect is due to the 90-degree off-axis polarization of the emitted LEDs (either target light 55 and/or alignment light(s) 20). This provides stereo optics for the user as he/she approaches and makes contact with the patient's eye during pre-marking. Stereo vision allows for depth of field and instrument location spatially with respect to the patient's corneal surface. Controlled contact with the cornea would be difficult, if not impossible, without stereo view. In addition to the polarized lens 40, short pass filter 30 is mounted at the optimal angle to reflect most, if not all, light emitted by target light 55 to the patient for a fixation target aligned directly with the user's visual axis. Target light 55 is not visible by the user and thus it does not obstruct the view of the patient's eye.

FIG. 4B illustrates how alignment lights 20 can be seen with the user's dominant eye but are blocked from the non-dominant eye via polarized lens 30.

In other embodiments, other mechanisms to block light to one or both eyes are used, including but not limited to red-green lenses, shutter mechanisms, and housings with long light paths that avoid user or patient visibility by the non-dominant eye. Some embodiments include a LED fixation light with a narrow beam and/or a flange, so that the patient's non-operative eye cannot easily see the fixation light. Further embodiments could be applied to the operative microscope rather than surgical loupes. When the surgeon is viewing the eye with a surgical microscope, the same phenomenon can still occur with these virtual Purkinjie light reflexes, resulting in the surgeon looking with the wrong eye due to cross fixation that some persons exhibit. During surgery, the eye surgeon may wish at times to confirm the alignment of structures within the eye or on the cornea, which requires the patient to look in precisely the same location eye-to-eye along their simultaneous visual axis pathways.

Figure 5:
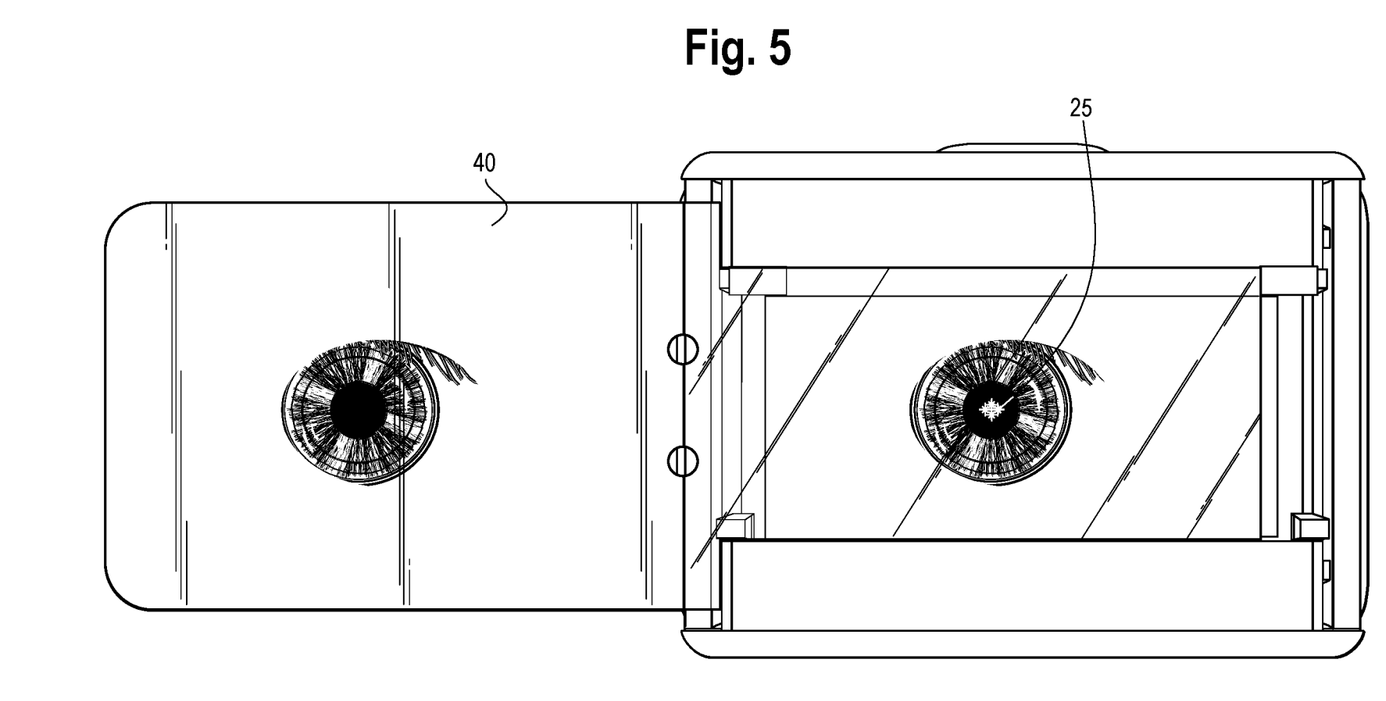
FIG. 5 is an elevation view showing the back of marking glasses when they are in use.

FIG. 5 is an elevation view showing the back of marking glasses 100 when they are in use. FIG. 5 depicts the unobstructed view of the patient's eye and shows the precise reflecting vertical and horizontal alignment rays 25 which are caused by alignment lights 20. This setup allows centration of the corneal marker with respect to the patient's visual axis. The corneal surface is clearly visible by both dominant and non-dominant eyes while the alignment rays 25 are visible only to the dominant eye.

Figure 6A:
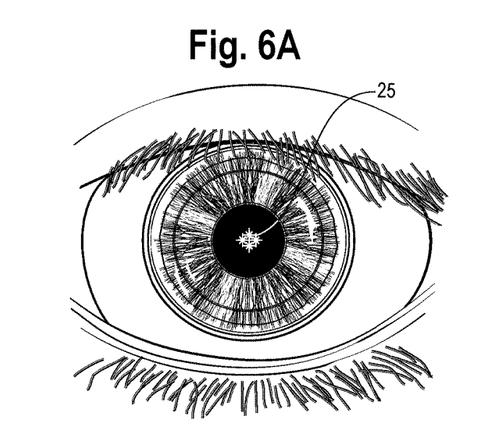
FIG. 6A represents a magnified user's view through marking glasses.
Figure 6B:
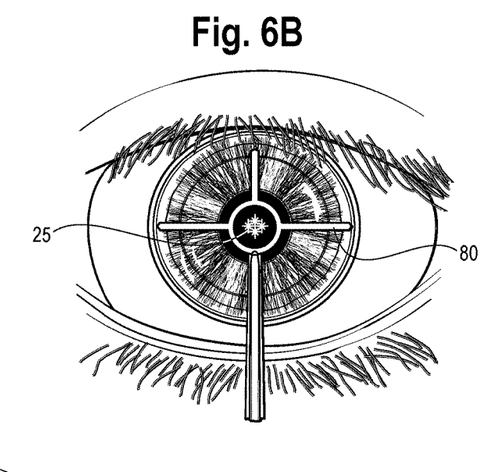
FIG. 6B represents a magnified user's-view through marking glasses with a marker being placed on the patient's cornea.
Figure 6C:
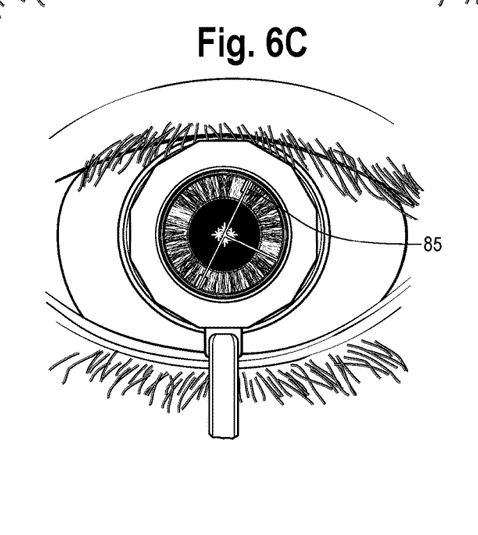
FIG. 6C represents an additional magnified user's-view through marking glasses with a Steep Meridian marker placed on the patient's cornea.

FIG. 6A-6C are images that represent a magnified user's view through marking glasses 100.

In FIG. 6A, the four alignment lights 20 are reflected on the surface of the patient's cornea, as he or she fixates his or her vision on target 50. This provides corneal reflexes precisely aligned with the patient's visual axis. Accurate placement of corneal markers is now achievable.

FIG. 6B represents a magnified user's-view through marking glasses 100 with marker 80 placed on the patient's cornea. Alignment rays 25 are marked for aiding precision surgical procedures requiring precise alignment.

FIG. 6C represents an additional magnified user's-view through marking glasses 100 with Steep Meridian marker 85 placed on the patient's cornea. Steep Meridian reference lines are marked for aiding surgical procedures requiring precise alignment with unnecessary translation from the vertical/horizontal to the patients calculated Steep Meridian.

Figure 7:
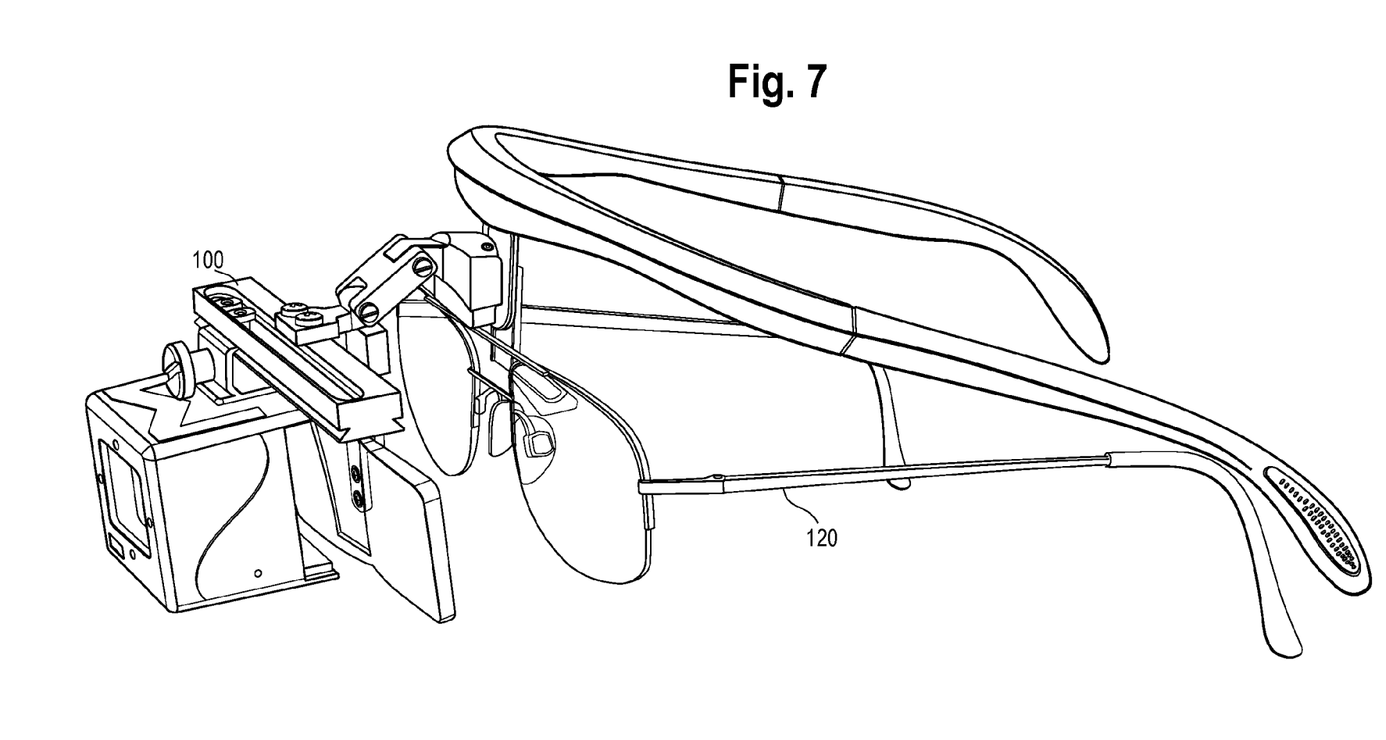
FIG. 7 is a perspective side view of marking glasses configured to be worn by a user wearing prescription glasses.

FIG. 7 is a perspective side view showing marking glasses 100 attached to a user's current glasses. In this embodiment, the user can wear marking glasses 100 over existing eyewear 120. In some embodiments, existing eyewear 120 are prescription glasses. This allows the user to benefit from their specific refractive correction. This also allows full adjustability for proper alignment with user's visual axis.

Magnifying lenses 90 can be rated in diopters and offer various corrective powers to enhance the visual clarity, power and desired working distance of the user. In some embodiments, telescopic surgical loops can be used instead of magnifiers 90.

Before use, the user can loosen the slide assembly (not shown). In some embodiments, the slide assembly includes a nut that can be loosened to allow the user to set target light 50 precisely over his own pupillary distance or diameter. This lateral movement allows for alignment lights 20 and/or target light 55 to be centrally aligned with the user's visual axis when focusing on a subject at the correct working distance for the lens chosen. This alignment validates the parallax-free, or at least reduced-parallax, function when the user is focusing on a subject with his or her dominant eye.

In some embodiments, to turn marking glasses 100 on, the user presses a power button (not shown). In some embodiments, marking glasses can be powered on via a remote signal and/or via voice control. In some embodiments, alignment lights 20 and/or target light 55 will remain on for a given amount of time, for example 90 seconds when the electronics of marking glasses 100 are turned on. In some embodiments, this given amount of time can be changed by the user and/or manufacturer.

Marking glasses 100 can also include a way to charge its battery. In some embodiments, marking glasses include USB connector 5. In some embodiments, USB connector 5 can also be used to transfer data from marking glasses 100. For example, in some embodiments, marking glasses 100 can include a camera that can record what the user is seeing as he is performing a surgery. This data can later be downloaded to a computer via USB connector 5.

In other or the same embodiments, marking glasses 100 can charge wirelessly via electromagnetic induction.

In one method of using marking glasses 100, a patient is asked to fixate on target 50. The user will view alignment lights 20 in a vertical/horizontal pattern centered on the patient's visual axis. At this time the user can center a preoperative marker with respect to reflex of alignment rays 25 and mark the cornea appropriately. The user will have advantage of using both eyes for stereo vision to maintain depth of field during marking.

While particular elements, embodiments and applications of the present invention have been shown and described, it will be understood that the invention is not limited thereto since modifications can be made by those skilled in the art without departing from the scope of the present disclosure, particularly in light of the foregoing teachings.

What is claimed is:

1. Zero parallax visual axis glasses for corneal pre-marking, the glasses comprising:
    (a) a target light;
    (b) a at least one alignment light, wherein said at least one alignment light is centrally aligned with a user's visual axis when focused on the cornea of a human subject;
    (c) a polarized lens; and
    (d) a short pass filter,
        wherein said target light and said at least one alignment light allow for alignment of the visual axis of said user with the visual axis of said human subject.

2. The pre-marking glasses of claim 1, wherein said target light is an LED.

3. The pre-marking glasses of claim 2, wherein said target light is red.

4. The pre-marking glasses of claim 2, wherein said target light is configured to blink.

5. The pre-marking glasses of claim 2, wherein said alignment light is configured to blink.

6. The pre-marking glasses of claim 1, wherein said alignment light is an LED.

7. The pre-marking glasses of claim 6, wherein said alignment light is white.

8. The pre-marking glasses of claim 1, wherein said polarized lens is configured for placement over a user's non-dominant eye.

9. The pre-marking glasses of claim 1, wherein said polarized lens is configured to block light originating from said alignment light.

10. The pre-marking glasses of claim 1, wherein said polarized lens is configured to block light originating from said target light.

11. The pre-marking glasses of claim 1, wherein said short pass filter is configured to prevent light originating from said targeting light from reaching a user.

12. The pre-marking glasses of claim 1, wherein said marking glasses are configured to fit over a pair of traditional prescription glasses.

13. A pair of pre-marking glasses configured to fit over a part of traditional prescription glasses comprising:
    (a) a target light, wherein said target light is a red LED configured to blink and wherein said target light is activated via voice control;
    (b) four alignment lights configured to form a cross, wherein each of said alignment lights is a white LED configured to blink and wherein said alignment lights are centrally aligned with a user's visual axis when focused on the cornea of a human subject;
    (c) a polarized lens configured for placement over a user's non-dominant eye to block light originating from said alignment lights and said target light;
    (d) a short pass filter configured to prevent light originating from said target light from reaching a user; and
    (e) a video camera,
        wherein said target light and said alignment lights allow for alignment of the visual axis of said user with the visual axis of said human subject.

14. A pair of zero parallax visual axis glasses for corneal pre-marking, said glasses comprising:
    (a) a target light, wherein said target light is a red LED configured to blink, wherein said target light is activated via voice control;
    (b) an alignment light, wherein said alignment light is a white LED;
    (c) a polarized lens; and
    (d) a short pass filter configured to prevent light originating from said targeting light from reaching a user.

15. The pair of zero parallax visual axis glasses of claim 14 further comprising:
    (e) a video camera.

* * * * *